US012544478B1

(12) United States Patent
Gao et al.

(10) Patent No.: US 12,544,478 B1
(45) Date of Patent: Feb. 10, 2026

(54) AROMA DIFFUSER

(71) Applicant: SHENZHEN SUNTEK ELECTRONIC CO., LTD., Shenzhen (CN)

(72) Inventors: Yong Gao, Shenzhen (CN); Haibo Ding, Shenzhen (CN)

(73) Assignee: SHENZHEN SUNTEK ELECTRONIC CO., LTD., Shenzhen (CN)

( * ) Notice: Subject to any disclaimer, the term of this patent is extended or adjusted under 35 U.S.C. 154(b) by 0 days.

(21) Appl. No.: 19/190,574

(22) Filed: Apr. 25, 2025

(30) Foreign Application Priority Data

Feb. 12, 2025 (CN) ......................... 202520228973.4

(51) Int. Cl.
*A61L 9/14* (2006.01)
*B05B 17/00* (2006.01)

(52) U.S. Cl.
CPC ............ *A61L 9/14* (2013.01); *B05B 17/0646* (2013.01); *A61L 2209/11* (2013.01); *A61L 2209/132* (2013.01); *A61L 2209/133* (2013.01)

(58) Field of Classification Search
CPC .. A61L 9/14; A61L 2209/11; A61L 2209/132; A61L 2209/133; B05B 17/0646
See application file for complete search history.

(56) References Cited

U.S. PATENT DOCUMENTS

2005/0077376 A1* 4/2005 Hess ......................... A61L 2/18 239/128
2015/0129681 A1* 5/2015 Kawano ................ A01M 1/205 239/102.2
2022/0378964 A1* 12/2022 Kawasaki ................. F24F 8/24

* cited by examiner

*Primary Examiner* — Brendan A Hensel
(74) *Attorney, Agent, or Firm* — Cheng-Ju Chiang

(57) ABSTRACT

An atomizing assembly and atomizer thereof provided in the present invention. The atomizing assembly includes first functional sheet, second functional sheet and first transducer which are arranged adjacently. The first functional sheet defines a liquid through hole, the second functional sheet defines atomization micropores, and the first transducer defines a first through hole. The liquid through hole is connected to the second functional sheet, and atomization micropores are connected to the first through hole. The atomizing assembly is electrically connected to the control circuit board, mouth of the liquid storage bottle is connected to the atomizing assembly for the liquid entering the liquid through hole. The second functional sheet and the first transducer cooperate to realize atomizing and injection function. The first functional sheet reduces the pressure of the liquid on the second functional sheet, reducing the possibility of oil leakage from the second functional sheet.

10 Claims, 8 Drawing Sheets

AROMA DIFFUSER

CROSS REFERENCE TO RELATED APPLICATIONS

The present invention is 35 U.S.C. § 119 benefit of earlier filing dates and rights of priority of Chinese Applications No. 202520228973.4 filed on Feb. 12, 2025, the disclosure of which is incorporated by reference herein.

BACKGROUND OF THE INVENTION

Field of the Invention

The present invention relates to the field of ultrasonic atomization, and more particularly, to an atomizing assembly and an atomizer.

Description of Related Art

A tomizers use ultrasonic vibration equipment to generate high-frequency vibrations to decompose liquid molecules into cold mist with a small molecular diameter and emit for atomization. They can be used in humidifiers, aroma diffusers (aromatherapy machines), etc. to humidify ambient air or emit aromatherapy essential oils. For example, the aroma diffuser uses ultrasonic vibrations to decompose liquid mixed with water and aromatherapy essential oil into nanoscale cold mist with a diameter of 0.1-5 microns and emit it into the surrounding air, making the air full of fragrance. This aroma diffuser is suitable for various places such as homes, hotel rooms, lobbies, corridors, and guest rooms. The atomizer assembly in the existing aroma diffuser will leak oil due to the pressure from the liquid in the liquid storage bottle; oil leakage causes the loss of precious aromatherapy essential oils, block atomizer assembly to be unable to emit mist, and oil pollution in the surrounding structure difficult to handle, etc., which brings a lot of trouble to users. Moreover, the more or less liquid in the liquid storage bottle exerts different pressures on the atomizing assembly, and the size of the sprayed mist is different, and the spray effect is unstable.

Therefore, it is necessary to provide an atomizing assembly which is not affected by liquid pressure, has smooth mist discharge without blockage, does not leak liquid or oil, has a stable structure, and has normal mist discharge.

SUMMARY OF THE INVENTION

An object of the present invention is to provide an atomizing assembly and an atomizer with smooth mist discharge and low leakage.

An atomizing assembly provided by the present invention, comprises a first functional sheet, a second functional sheet and a first transducer that are adjacently arranged. The first functional sheet defines a liquid through hole, the second functional sheet defines atomization micropores, and the first transducer defines a first through hole in the center. The liquid through hole of the first functional sheet is connected to the second functional sheet, and the atomization micropores of the second functional sheet are connected to the first through hole. The second functional sheet and the first transducer cooperate to realize the liquid atomization and injection function, and the first functional sheet can transport liquid to the second functional sheet.

Due to the presence of the first functional sheet, the pressure from the liquid in a liquid storage bottle is reduced, that is, the pressure of the liquid on the second functional sheet is reduced, which greatly reduces the possibility of oil leakage from the second functional sheet (usually used for atomization function).

In some embodiments, the first transducer may be fitted with one side of the second functional sheet close to the first functional sheet or fitted with the other side of the second functional sheet away from the first functional sheet. In some specific embodiments, when the first transducer is arranged on the side of the second functional sheet close to the first functional sheet, the liquid through hole of the first functional sheet is arranged at least partially opposite to the first through hole, and the first through hole exposes the second functional sheet to face the first functional sheet, so that liquid can pass through the liquid through hole of the first functional sheet and contact the second functional sheet. The first transducer cooperates with the second functional sheet to realize an atomization function, so that the liquid entering the liquid through hole and contacting one side of the second functional sheet is atomized and then output from the other side of the second functional sheet; In some specific embodiments, further, the size of the first functional sheet can be set to be relatively smaller, so that while the first functional sheet is partially fitted with the second functional sheet, the first transducer can also be fitted with the remaining part of the second functional sheet, and the liquid through hole of the first functional sheet is arranged at a position opposite to the part of the second functional sheet exposed by the first through hole, and liquid can reach and contact the second functional sheet through the liquid through hole.

In some other embodiments, the first transducer is arranged on the other side of the second functional sheet away from the first functional sheet, the first functional sheet is in contact with the second functional sheet, the liquid can pass through the liquid through hole of the first functional sheet and then contact the second functional sheet, and the first transducer cooperates with the second functional sheet to realize an atomization function, so that the liquid entering the liquid through hole and contacting one side of the second functional sheet is atomized and then output from the other side of the second functional sheet.

In some specific embodiments, the size of the liquid through hole can allow liquid to flow through, and its diameter of the liquid through hole can be set as desired, for example, 0.5 mm, 1 mm, or 2 mm. The larger the size of the liquid through hole, the faster the liquid enters, and the smaller the size, the slower the liquid enters. The size of the liquid through hole can be designed according to sizes of liquid molecules, a desired flow rate of the liquid entering the liquid through hole, a desired atomization speed and atomization amount.

In some embodiments, the second functional sheet is a metal sheet, and the first transducer is a piezoelectric ceramic transducer ring. The piezoelectric ceramic transducer ring and the metal sheet are combined to realize the atomization and spray function.

In some embodiments, the first functional sheet can be a metal sheet or a non-metal sheet.

In some embodiments, the first functional sheet and the second functional sheet are both metal sheets, and the two metal sheets can be welded together, glued together, or contact each other. The second functional sheet defines atomization micropores for the mist discharge function.

In some embodiments, the atomizing assembly further includes an assembly part, the assembly part is provided with an assembly hole, the first functional sheet, the second functional sheet, and the first transducer are axially stacked along the assembly hole and installed in the assembly part, and the liquid through hole and the first through hole are correspondingly connected to the assembly hole.

In some embodiments, the assembly part is a soft rubber ring with an annular assembly groove on the inner side wall, and the first functional sheet, the second functional sheet, and the first transducer are arranged in the assembly groove. The use of a soft rubber ring facilitates positioning and assembly while improving sealing performance.

In some embodiments, the second functional sheet and the first transducer are connected with a paired electronic wire. In a specific embodiment, the first transducer is connected with a first electronic wire (such as a positive wire), and the second functional sheet is connected with a paired second electronic wire (such as a negative wire). The electronic wires can be connected to the control circuit board of the atomizer and electrically connected to the power supply. When the atomization function is powered on, the second functional sheet and the first transducer are powered through the electronic wires, so that the second functional sheet generates ultrasonic vibration, thereby the liquid contacting the second functional sheet is atomized.

In some other embodiments, the atomizer assembly further includes a second transducer. the first transducer, the second functional sheet, and the second transducer are sequentially arranged in close contact, the second transducer is provided with a second through hole, the first through hole and the second through hole correspond to each other, the liquid through hole of the first functional sheet is arranged at least partially opposite to the first through hole, the first through hole is arranged at least partially opposite to the second through hole, the first through hole exposes the second functional sheet to face the first functional sheet, liquid can pass through the liquid through hole of the first functional sheet and contact the second functional sheet, the first transducer and the second functional sheet can cooperate to realize the atomization function, so that the liquid entering the liquid through hole and contacting one side of the second functional sheet is atomized and output from the other side of the second functional sheet. In some specific embodiments, the first functional sheet is a non-metallic sheet, the second functional sheet is a metal sheet, and the first functional sheet and the second functional sheet are bonded together. In other specific embodiments, the first functional sheet and the second functional sheet are metal sheets, the first transducer and the second transducer are piezoelectric ceramic transducer rings, and the two metal sheets can be welded together, glued together, or be fitted to (contact close to) each other.

In some embodiments, the first transducer and the second transducer are connected to a first electronic wire (such as a positive wire), and the second functional sheet is connected to a paired second electronic wire (such as a negative wire). In a specific embodiment, the electronic wires can be connected to the control circuit board of the atomizer and electrically connected to power source. When the atomization function is activated, the second functional sheet and the first transducer are powered on through the electronic wires, the second functional sheet generates ultrasonic vibrations, so that the liquid contacting the second functional sheet is atomized. In the embodiments, the first transducer and the second transducer are provided, and the atomization function and the atomization spraying strength of the second functional sheet can be enhanced.

In some embodiments, the first functional sheet and/or the second functional sheet is provided with a deformation portion, and a liquid storage chamber is formed between the first functional sheet and the second functional sheet at the position of the deformation portion. In some embodiments, the deformation portion is a protrusion or depression formed on the first functional sheet and/or on the second functional sheet. In other embodiments, the structural design of the deformation portion only needs to form a liquid storage chamber between the two metal sheets, and is not limited to a protrusion or a depression. In a specific embodiment, one of the first functional sheet and the second functional sheet is provided with a deformation portion, for example, if a deformation portion such as a depression is formed on the second functional sheet, a liquid storage chamber can be formed at a position corresponding to the depression after the second functional sheet is combined with the first functional sheet, and the liquid can temporarily stay in the liquid storage chamber after entering from the liquid through hole of the first functional sheet; or the same deformation portion is formed on the first functional sheet to form the liquid storage chamber; or the first functional sheet and the second functional sheet are both form deformation portions, wherein the first functional sheet and the second functional sheet respectively form a protrusion and a depression, or, both form protrusions, or both form depressions, and a height/depth of the protrusions or depressions along the axial direction is different, thereby, the protrusions or depressions of the first functional sheet and the second functional sheet are matched to form the liquid storage chamber. A liquid storage chamber is formed between the first functional sheet and the second functional sheet at the position corresponding to the deformation part. After power is turned on, the second functional sheet resonates with the first functional sheet at the same frequency, thereby the liquid in the bottle enters the liquid storage chamber stably. The liquid enters the liquid storage chamber through the liquid through hole in the first functional sheet, and the liquid pressure in the liquid storage chamber is reduced, which greatly reduces the possibility of oil leakage from the second functional sheet; and the liquid storage chamber can continuously provide stable low-pressure liquid to the second functional sheet facing the outside, so that the pressure inside and outside the second functional sheet is kept consistent, and no matter how much liquid is in the bottle, it can ensure continuous misting and stable misting, so that the spray is stable and not easy to be blocked.

In some embodiments, the liquid through hole is arranged at the deformation part of the first functional sheet, and the liquid directly enters the liquid storage chamber through the liquid through hole.

The present invention also provides an atomizer, which includes a liquid storage bottle, a control circuit board, and the atomizing assembly as described above. The electronic wires of the atomizing assembly are electrically connected to the control circuit board, and the liquid outlet of the liquid storage bottle is connected to the atomizing assembly to allow the liquid in the liquid storage bottle to flow to the liquid through hole of the first functional sheet.

In some embodiments, the atomizer further comprises a shell, the shell defines a first mist outlet, and the first through hole of the first transducer of the atomizing assembly is correspondingly connected to the first mist outlet.

In some embodiments, the atomizer further comprises a power supply assembly, the shell is provided with a power supply port, and the power supply assembly is arranged in the power supply port; a liquid inlet is formed at a top of the shell, a bottle mouth of the essential oil bottle extends into the liquid inlet and is detachably connected via an interface connector; the power supply assembly and the atomizing assembly are respectively electrically connected to the control circuit board.

The Advantages of the Present Invention are:

the atomizing assembly of the present invention is provided with the first functional sheet, so that the pressure from the liquid in the liquid storage bottle is reduced, that is, the pressure of the liquid on the second functional sheet is reduced, which greatly reduces the possibility of oil leakage of the second functional sheet (usually used for liquid atomization function).

Furthermore, a liquid storage chamber is formed between the first functional sheet and the second functional sheet at a position corresponding to the deformation portion. After power is turned on, the second functional sheet resonates with the first functional sheet at the same frequency, so that the liquid in the bottle enters the liquid storage chamber stably. The liquid enters the liquid storage chamber through the liquid through hole of the first functional sheet, and the liquid pressure in the liquid storage chamber is reduced, thereby greatly reducing the possibility of oil leakage from the second functional sheet. The liquid storage chamber can continuously provide the second functional sheet with stable low-pressure liquid, so that the pressure on the second functional sheet remains consistent, and the mist can be continuously discharged and the mist output is stable regardless of the amount of liquid in the bottle, so that the mist spray is stable and not easy to be blocked. The liquid entering the liquid through hole of the first functional sheet is further atomized into nano-scale particles through the second functional sheet, and is emitted through the first through hole, so that the emitted mist molecules can be finer.

DETAILED DESCRIPTION OF THE INVENTION

Figure 1:
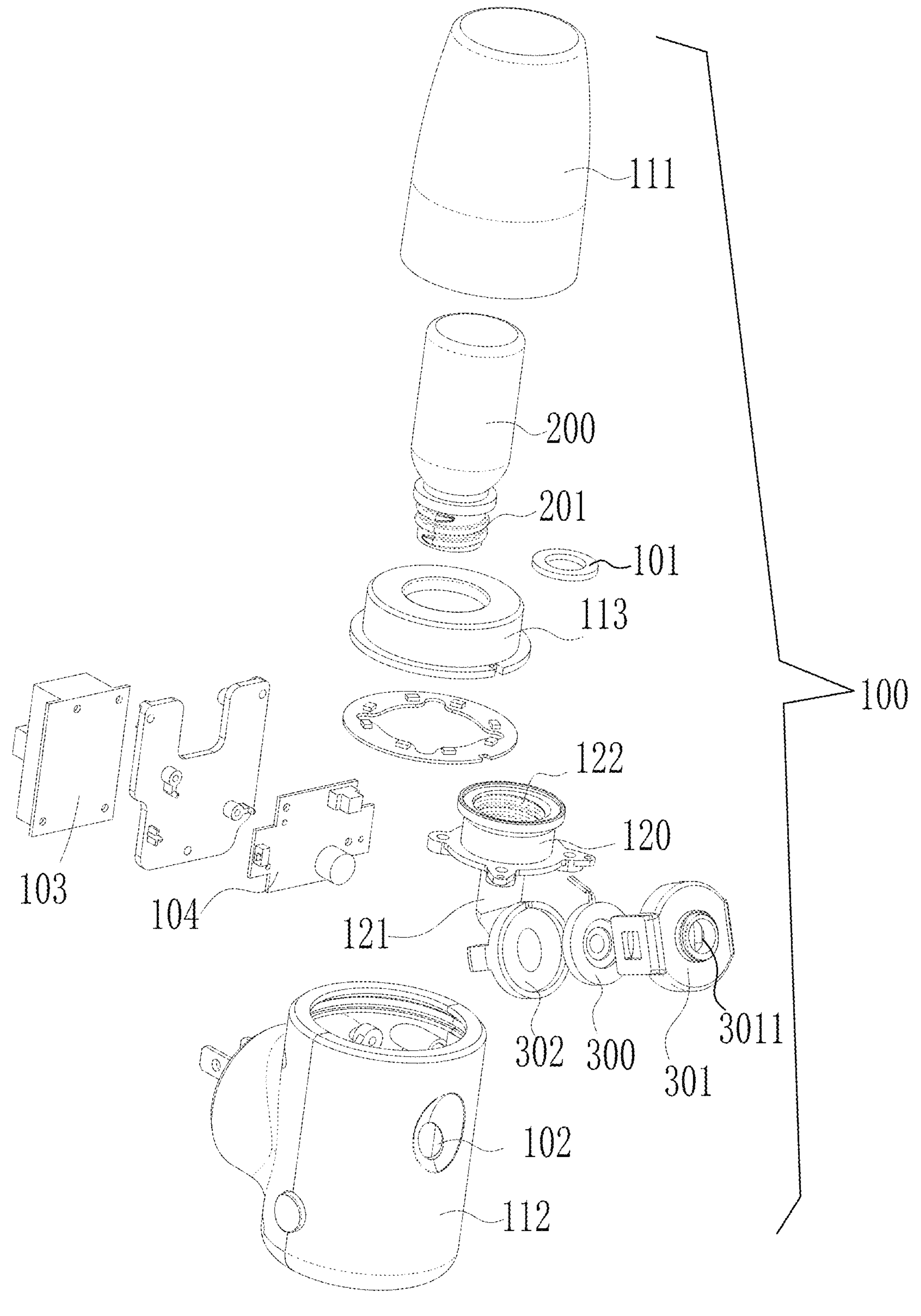
FIG. 1 illustrates a first exploded view of an atomizer in accordance with an embodiment of the present invention.
Figure 2:
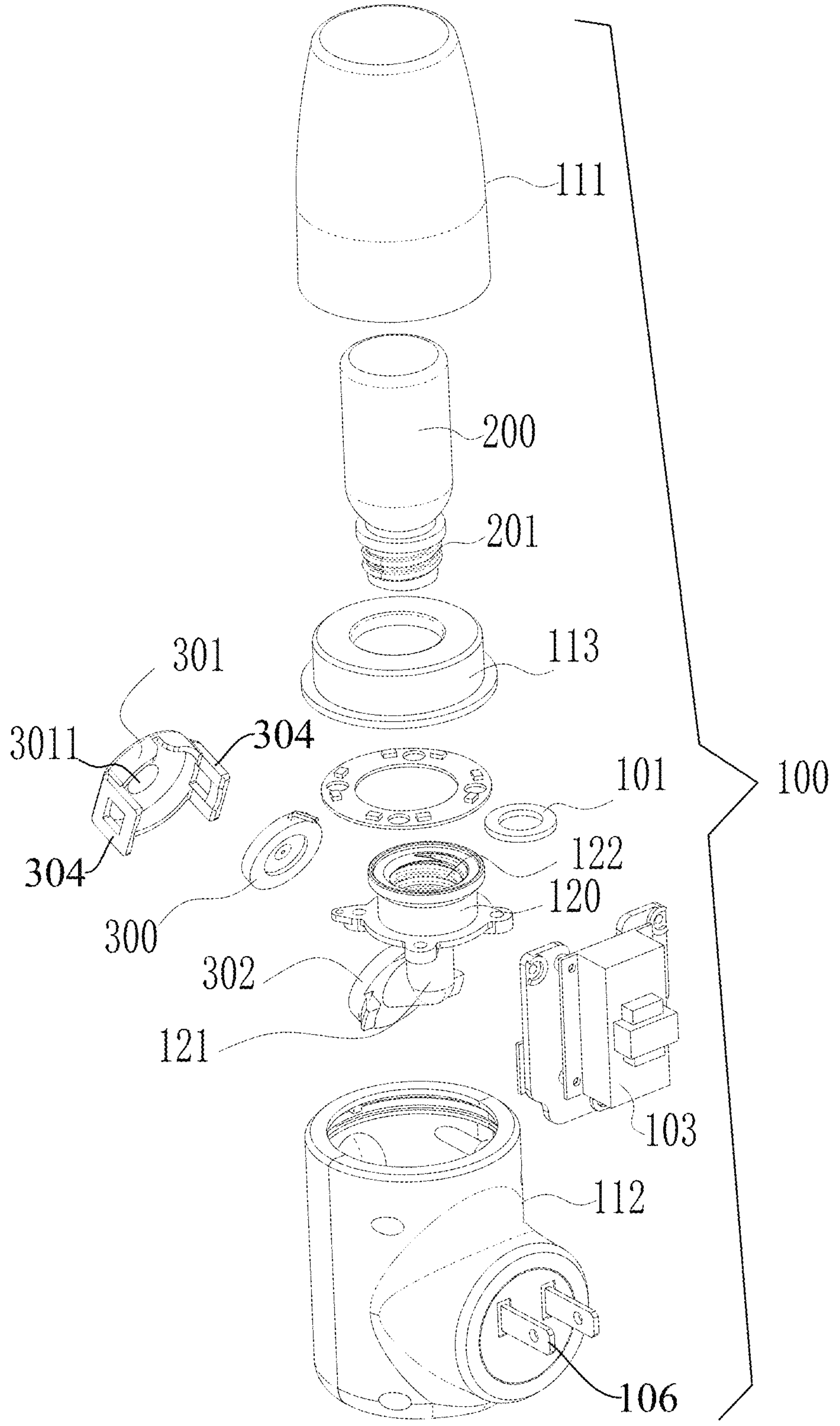
FIG. 2 illustrates a second exploded view of the atomizer in accordance with the embodiment of the present invention.
Figure 3:
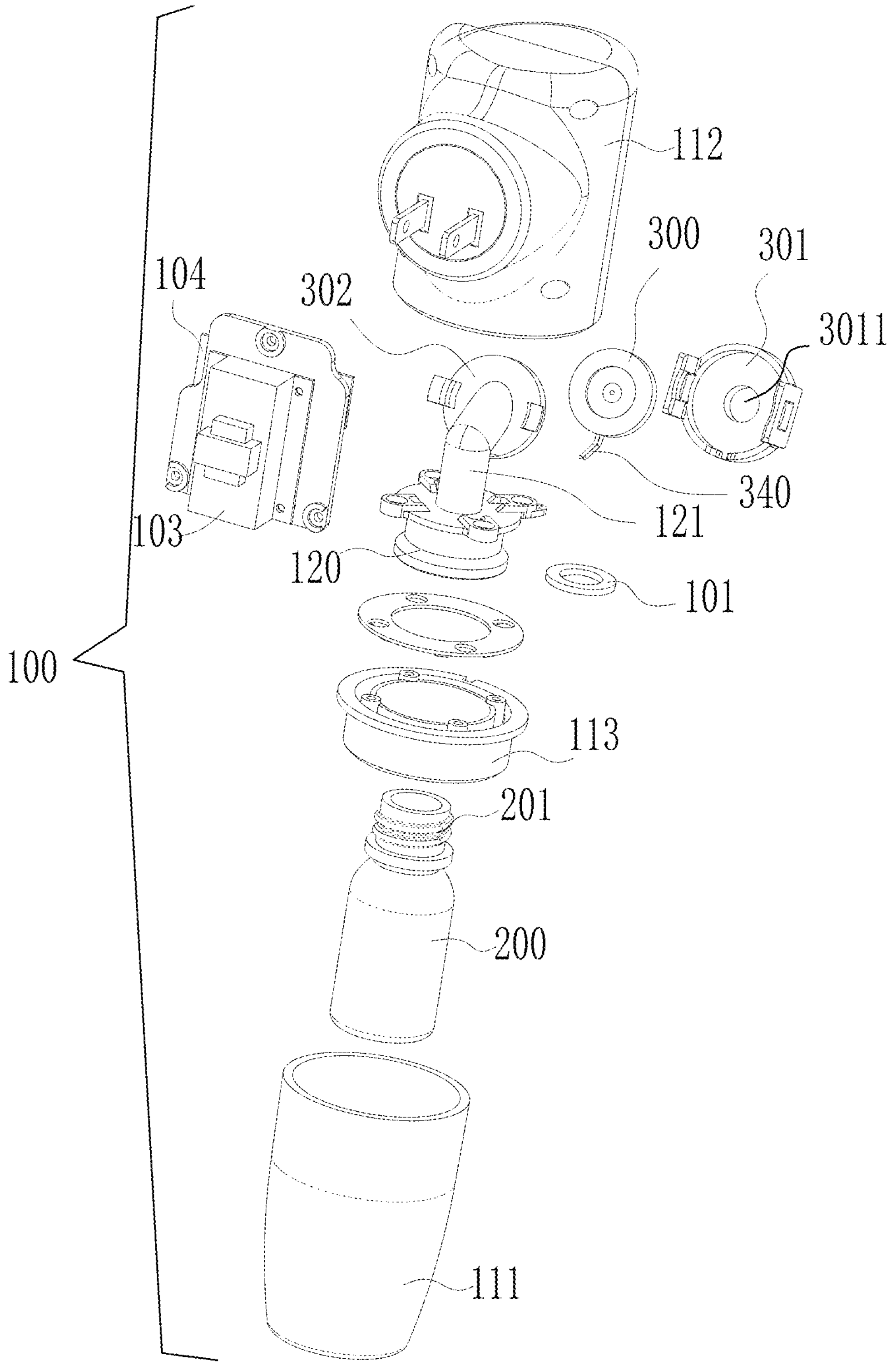
FIG. 3 illustrates a third exploded view of the atomizer in accordance with the embodiment of the present invention.
Figure 4:
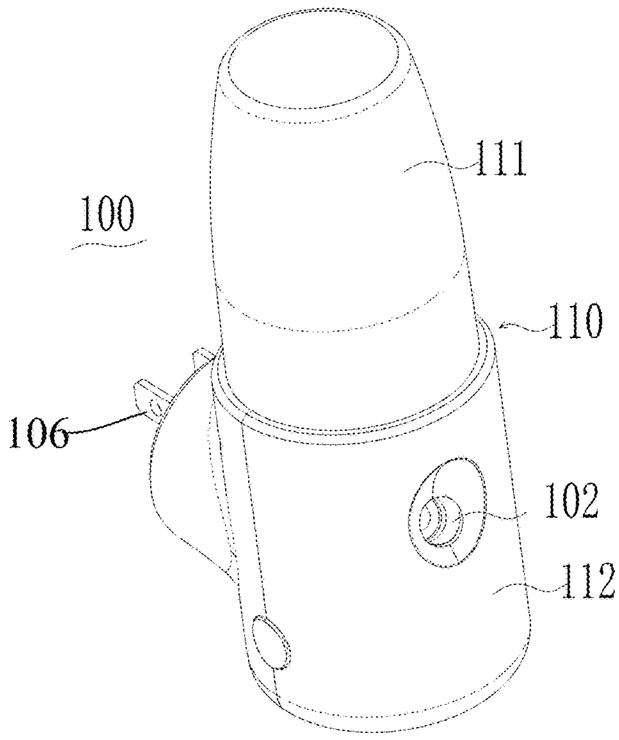
FIG. 4 illustrates a first perspective view of the atomizer in accordance with the embodiment of the present invention.
Figure 5:
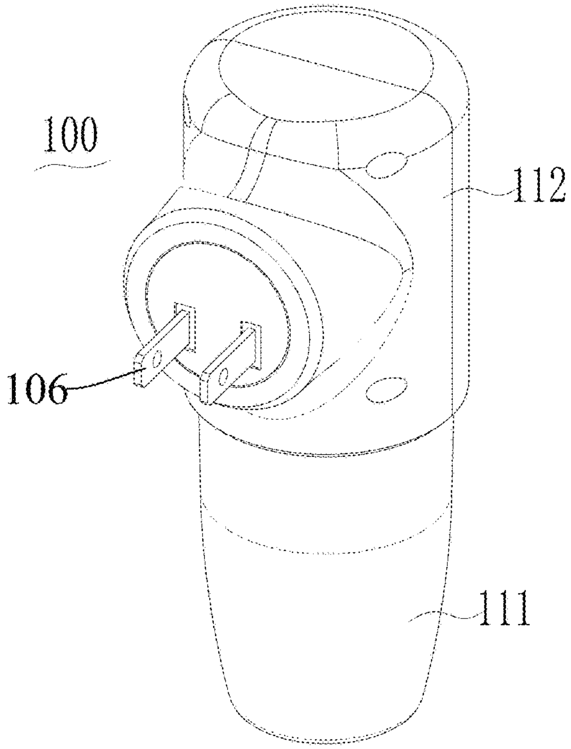
FIG. 5 illustrates a second perspective view of the atomizer in accordance with the embodiment of the present invention.
Figure 6:
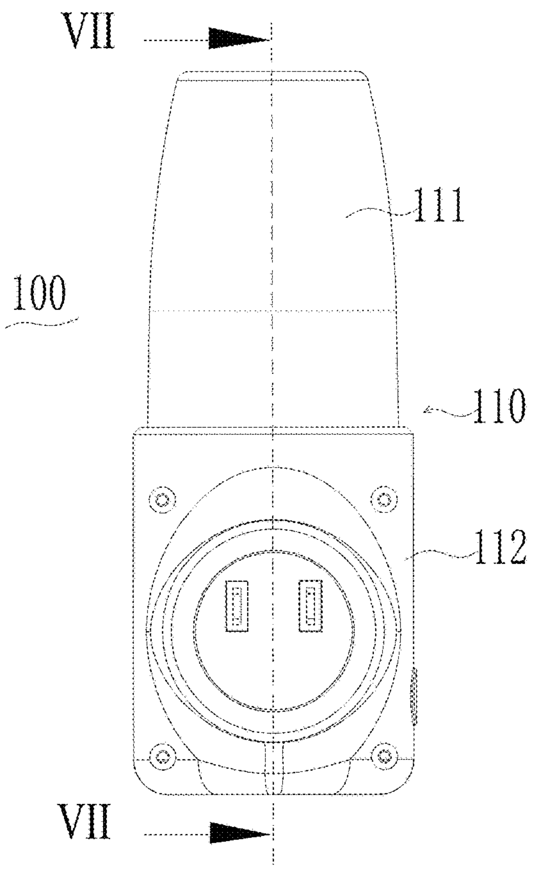
FIG. 6 illustrates a front view of the atomizer in accordance with the embodiment of the present invention.
Figure 7:
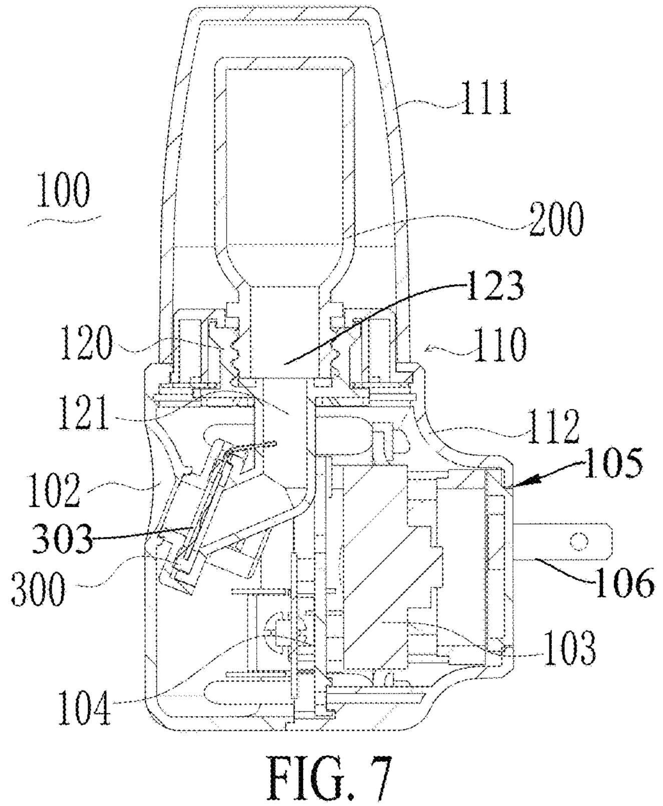
FIG. 7 illustrates a cross-sectional view along line VII-VII of FIG. 6.

Exemplary embodiments of the present invention will be described in more detail below with reference to the accompanying drawings. Although exemplary embodiments of the present invention are shown in the accompanying drawings, it should be understood that the present invention can be implemented in various forms and should not be limited by the embodiments described herein. On the contrary, these embodiments are provided to enable a more thorough understanding of the present invention and to fully convey the scope of the present invention to those skilled in the art.

It should be understood that the terminology used herein is for the purpose of describing specific example embodiments only and is not intended to be limiting. Unless the context clearly indicates otherwise, as used herein, the singular forms “a”, “an”, and “the” may also be intended to include the plural forms. The terms “comprise”, “include”, “contain”, and “have” are inclusive and thus specify the presence of the stated features, steps, operations, elements, and/or components, but do not preclude the presence or addition of one or more other features, steps, operations, elements, components, and/or combinations thereof. The method steps, processes, and operations described herein are not to be construed as necessarily requiring their performance in the particular order described or illustrated, unless explicitly identified as an order of performance. It should also be understood that additional or alternative steps may be used.

Although the terms “first”, “second”, etc. may be used in the text to describe multiple elements, components, regions, layers, and/or sections, these elements, components, regions, layers, and/or sections should not be limited by these terms. These terms may only be used to distinguish one element, component, region, layer, or section from another region, layer, or section. Unless the context clearly indicates otherwise, terms such as “first,” “second,” and other numerical terms do not imply a sequence or order when used in the text. Therefore, the first elements, components, regions, layers, or sections discussed below may be referred to as second elements, components, regions, layers, or sections without departing from the teachings of the example embodiments.

For ease of description, spatially relative terms may be used herein to describe the relationship of one element or feature relative to another element or feature as shown in the figures, such as “inside”, “outside”, “inner side”, “outer side”, “below”, “beneath”, “over”, “above”, “front end”, “rear side”, etc. Such spatially relative terms are intended to include different orientations of the device during use or operation in addition to the orientation depicted in the figures. For example, if the device in the figures is turned over, elements described as “below” or “beneath” other elements or features would then be oriented “above” or “over the other elements or features.” Thus, the example term “below” can encompass both an orientation of above and below. The device may be otherwise oriented (rotated 90 degrees or at other orientations) and the spatially relative descriptors used herein interpreted accordingly.

In order to illustrate the technical solution described in present invention, a specific embodiment is provided below.

Please refer to FIGS. 1 to 7, an atomizer 100 in accordance with an embodiment of the present invention includes a shell 110, a liquid storage bottle 200, a control circuit board 104, and an atomizer module. The atomizer 100 in this embodiment is specifically an aroma diffuser, and the liquid storage bottle 200 can contain aromatherapy essential oils therein. The shell 110 includes an upper cover 111 in a shape of a hollow cylinder, a circular middle cover 113, and a bottom cover 112 in a shape of a hollow cylinder. The middle cover 113 can be detachably installed between the upper cover 111 and the bottom cover 112, and can be accommodated in the space formed by the upper cover 111 and the bottom cover 112. The middle cover 113 defines a central opening, and the atomization module includes an interface connector 120. External threads 201 are formed around outer side of a bottle mouth of the liquid storage bottle 200. One end of the interface connector 120 forms an annular wall and can accommodate the bottle mouth of the liquid storage bottle 200 and is provided with matching internal threads 122, and the other end extends outwardly to be connected with a liquid guide pipe 121, the connector 120 defines a liquid channel 123 therein which is communicated with the liquid storage bottle 200. The bottle mouth of the liquid storage bottle 200 extends into the interface connector 120 through the opening of the middle cover 113, and the external threads 201 of the bottle mouth of the liquid storage bottle 200 is threadedly connected with the internal threads 122 of the interface connector 120, thereby realizing a detachable connection. A rubber ring 101 is provided between the connection between the external threads of the bottle mouth of the liquid storage bottle 200 and the internal threads of the interface connector 120 to prevent the liquid of the liquid storage bottle 200 from leaking out; the interface connector 120 can be fixed in the shell 110 by threads or screws.

Figure 8:
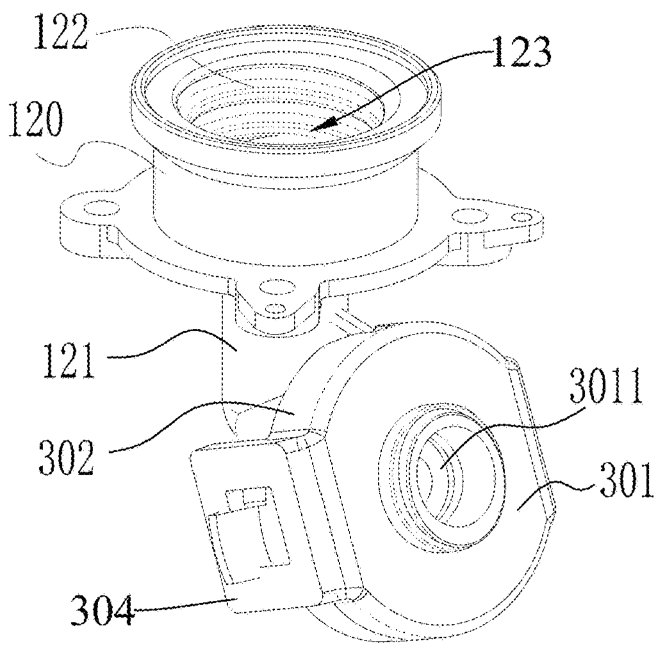
FIG. 8 illustrates a perspective view of an atomization module of the atomizer in accordance with the embodiment of the present invention.
Figure 9:
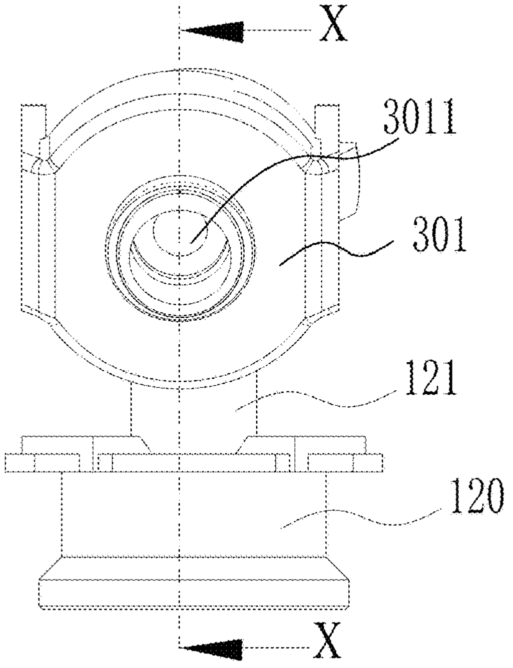
FIG. 9 illustrates a front view of the atomization module of the atomizer in accordance with the embodiment of the present invention.
Figure 10:
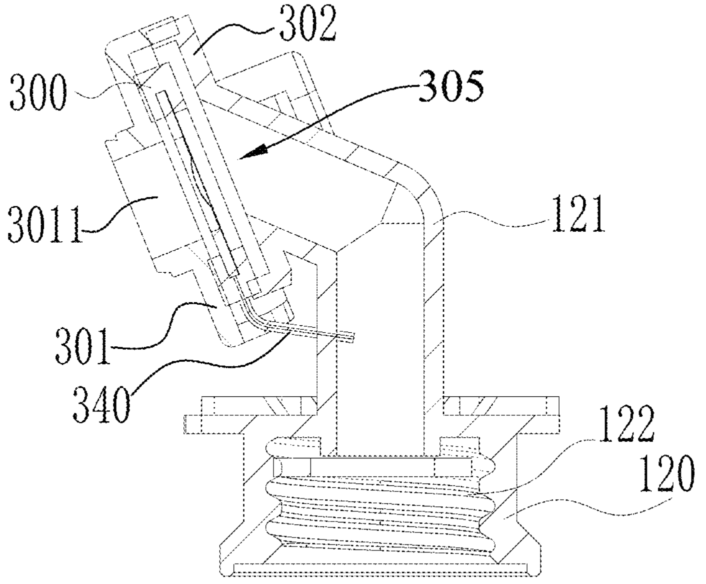
FIG. 10 illustrates a cross-sectional view along line X-X of FIG. 9.

Referring to FIGS. 8 to 10, the atomization module includes an atomizing assembly 300, a front pressure plate 301 and a rear pressure plate 302. The front pressure plate 301 and the rear pressure plate 302 are snap-connected to each other, are circular, fasten by side buckles 304 and installed in the bottom cover 112. The rear pressure plate 302 defines a hole 305 therethrough in communication with the liquid guide pipe 121. An atomizing cavity 303 is formed between the front pressure plate 301 and the rear pressure plate 302 to accommodate the atomizing assembly 300. The front pressure plate 301 and the rear pressure plate 302 are detachably connected to facilitate replacement of the atomizing assembly 300. One end of the liquid guide pipe 121 is connected to the interface connector 120, and the other end is connected to the rear pressure plate 302. The bottle mouth of the liquid storage bottle 200 is communicated with the interface connector 120 and the liquid guide pipe 121, and the liquid guide pipe 121 is communicated with the atomizing cavity 303 formed between the front pressure plate 301 and the rear pressure plate 302; the bottle mouth of the liquid storage bottle 200 is arranged downward, and the gravity of the liquid in the liquid storage bottle 200 and the guiding effect of the liquid guide pipe 121 are utilized to make the liquid in the liquid storage bottle 200 flow to the atomizing cavity 303 between the front pressure plate 301 and the rear pressure plate 302 through the liquid guide pipe 121, and the atomizing assembly 300 is arranged in the atomizing cavity 303. After the liquid flows into the atomizing cavity 303, it will contact the atomizing assembly 300, so that the atomizer can be used in conjunction with a liquid storage bottle (essential oil bottle), thereby extending the use time.

The liquid guide pipe 121 can be a fixed-shape tube body, which can be designed with a bent/curved angle to facilitate guiding the liquid in the upper liquid storage bottle to a direction that fully contacts the atomizing assembly. The bent/curved angle can be set according to actual needs without limitation. The liquid guide pipe 121 can also be a liquid guide hose with adjustable length and curvature, which can very conveniently adjust the length and size of the liquid flow path and the spray angle. And because the liquid guide pipe 121 can store essential oils, when the liquid storage bottle is replaced, the atomizing assembly can also normally contact the essential oil to produce fragrant mist, ensuring the normal operation of the aroma diffuser. The liquid guide pipe 121 can be integrally formed with the rear pressure plate 302 and the interface connector 120, or can be installed together in a detachable connection manner without limitation.

The shell 110 defines a first mist outlet 102 for discharging fragrant mist out of the shell 110 and defines a power port 105 for installing a power plug 106, and the atomization module is covered on the first mist outlet 102. A power supply assembly 103 is provided in the shell 110. The power supply assembly 103 is installed behind the power port 105; the power supply assembly 103 is integrated into the power port of the shell 110, which has a compact structure and saves components, while avoiding the battery oxidation problem in the prior art, which is scientific and reasonable, and prolongs the service life of the aroma diffuser. The shell 110 defines a mounting groove (not shown) for fixing the control circuit board 104, and the control circuit board 104 is mounted in the mounting groove, and the power supply assembly 103 and the atomization module are electrically connected to the control circuit board 104 respectively.

Figure 11:
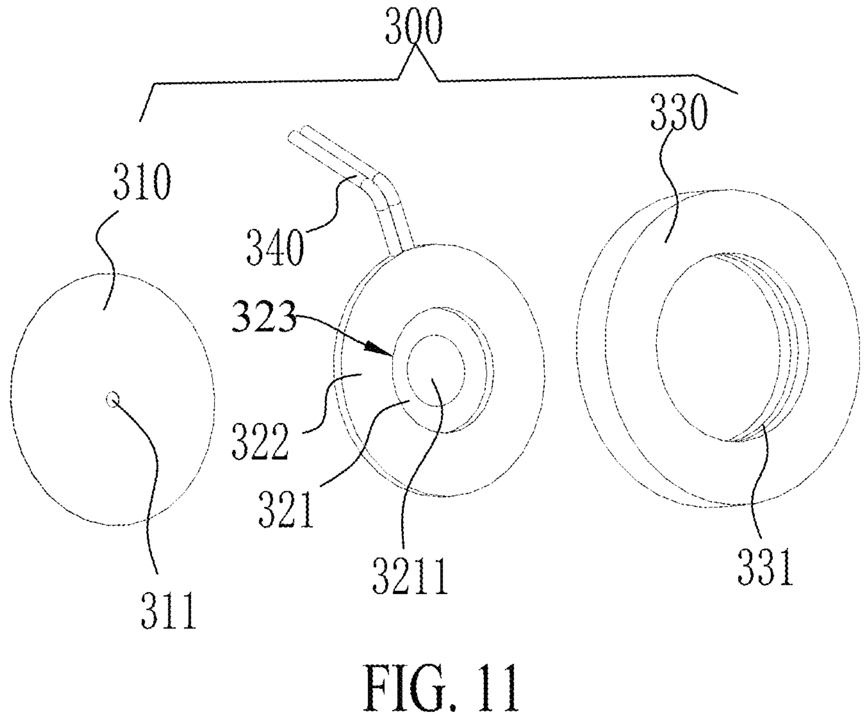
FIG. 11 illustrates an exploded view of an atomizing assembly of the atomizer in accordance with the embodiment of the present invention.
Figure 12:
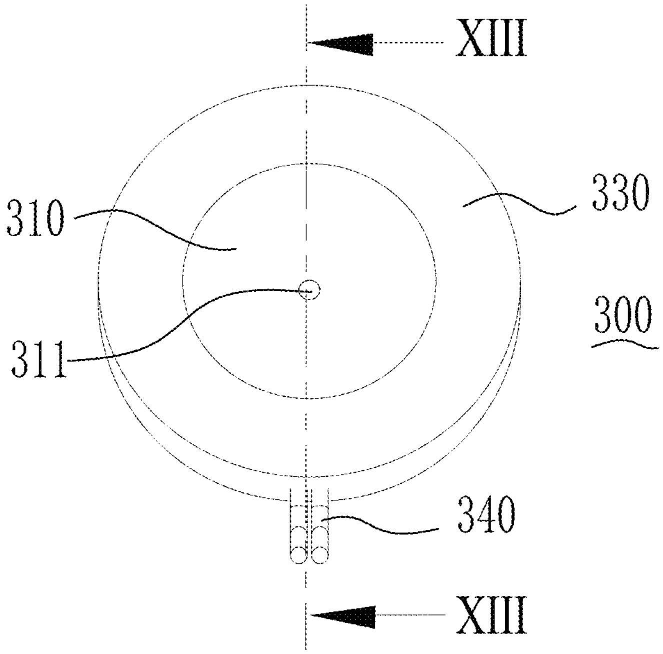
FIG. 12 illustrates a perspective view of the atomizing assembly of the atomizer in accordance with the embodiment of the present invention.
Figure 13:
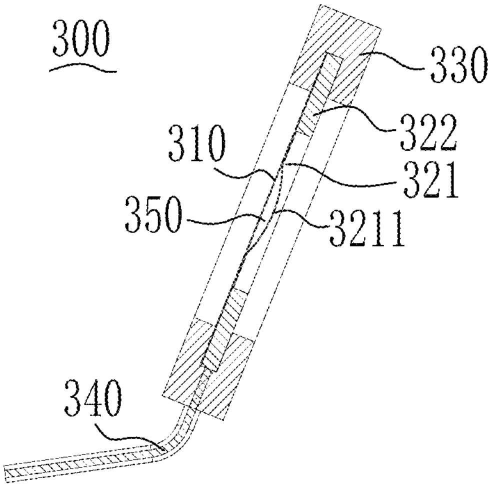
FIG. 13 illustrates a cross-sectional view along line XIII-XIII of FIG. 12.

With reference to FIGS. 11 to 13, in one embodiment, the atomizing assembly 300 includes a first functional sheet 310, a second functional sheet 321 and a first transducer 322. The first functional sheet 310 in this specific embodiment is a metal sheet with a liquid through hole 311 in the center. The first functional sheet 310 is attached to the second functional sheet 321. The second functional sheet 321 and the first transducer 322 are combined to realize the atomization function. Specifically, the second functional sheet 321 is made of a metal sheet, and the first transducer 322 is a ceramic transducer ring. The second functional sheet 321 and the first transducer 322 are connected to a paired electronic wire 340 to electrically connect the control circuit board 104. Specifically, the first transducer 322 is connected to a positive electronic wire, and the second functional sheet 321 is connected to a paired negative electronic wire. In other embodiments, the first functional sheet 310 can be made of a non-metallic material. The first functional sheet 310 can be attached to the second functional sheet 321 by various ways such as pasting and welding.

In this embodiment, the first functional sheet 310 and the second functional sheet 321 are conductive, and the first functional sheet 310 defines the liquid through hole 311. In a specific embodiment, the first functional sheet 310 and the second functional sheet 321 are both metal sheets, and the two metal sheets can be welded together, or glued together, or fitted with (close contact) each other. The first transducer 322 is a piezoelectric ceramic transducer ring; the first transducer 322 defines a first through hole 323 in the center, and the liquid through hole 311 in the first functional sheet 310 is at a position opposite to the second functional sheet 321, so that the liquid entering the liquid through hole 311 can contact the second functional sheet 321. The second functional sheet 321 defines atomization micropores, and the atomization micropores are arranged at positions corresponding to the first through holes of the ceramic transducer ring, so that the liquid is atomized and sprayed outward from the atomization micropores.

Due to the provision of the first functional sheet 310, the pressure of the liquid in the liquid storage bottle 200 is reduced, that is, the pressure of the liquid on the second functional sheet 321 is reduced, which greatly reduces the possibility of oil leakage of the second functional sheet 321 (which is usually used for atomization function).

In another embodiment (not shown), the atomizing assembly further includes a second transducer, the first transducer, the second functional sheet, and the second transducer are sequentially arranged in close contact, the second transducer is provided with a second through hole, the first through hole and the second through hole correspond to each other, the liquid through hole of the first functional sheet is arranged at least opposite to a portion of the first through hole, the first through hole is arranged at least opposite to a portion of the second through hole, the second through hole exposes the second functional sheet and is opposite to the first functional sheet, and the liquid can pass through the liquid through hole of the first functional sheet and contact the second functional sheet. The first transducer, the second transducer and the second functional sheet cooperate to realize the atomization function, so that the liquid entering the liquid through hole and contacting one side of the second functional sheet is atomized and output from the other side of the second functional sheet and transported out through the second through hole. In some specific embodiments, the first functional sheet and the second functional sheet are metal sheets, the first transducer and the second transducer are piezoelectric ceramic transducer rings, the two metal sheets can be welded together, or glued together, or fitted (close contact) together, and the two piezoelectric ceramic transducer rings are fitted on both sides of the second functional sheet. The first functional sheet and the second functional sheet, at their middle portions, are exposed through the second through hole, and the exposed portions are fitted with each other. In a specific embodiment, the first functional sheet can be designed to be slightly smaller so that the first functional sheet fits the second functional sheet while the annular second transducer also fits the second functional sheet.

The atomizer assembly 300 further includes an assembly part 330, and the assembly part 330 defines a central hole. In one embodiment, the first functional sheet 310, the second functional sheet 321 and the first transducer 322 are sequentially stacked along the axial direction of the central hole and installed in the assembly part 330, and the first through hole of the first transducer 322 is correspondingly connected to the central hole of the assembly part 330. In this embodiment, the assembly part is a soft rubber ring (also indicated as the reference number 330) with an annular assembly groove 331 on the inner side wall, and the first functional sheet 310, the second functional sheet 321 and the first transducer 322 are installed in the assembly groove 331. The use of a soft rubber ring makes it easy to position and assemble while improving the sealing performance. The rubber ring 330 tightly fixes and seals peripheries of the first functional sheet 310, the second functional sheet 321 and the first transducer 322. The first functional sheet 310, the second functional sheet 321 and the first transducer 322 are resonantable at the same frequency.

Specifically, the electronic wire 340 can be connected to the control circuit board 104 of the atomizer and electrically connected to the power supply. When the atomizer is powered on and the atomization function is started, the second functional sheet 321 and the first transducer 322 are powered via the electronic wire 340, so that the second functional sheet 321 generates ultrasonic vibrations. The liquid first passes through the liquid through hole 311 of the first functional sheet 310, is atomized under the ultrasonic vibration of the second functional sheet 321 and is sprayed from the atomization micropores of the second functional sheet 321. Due to the presence of the first functional sheet 310, liquid flow slows down, liquid pressure on the second functional sheet 321 is reduced, the possibility of oil leakage of the second functional sheet 321 (usually used for the atomization function) is greatly reduced. The liquid is formed into fine molecules under the ultrasonic vibration of the second functional sheet 321, and then atomized into nano-scale particles and sprayed out through the first through holes.

In some other embodiments, the first functional sheet 310 combines a ceramic transducer ring to form a structure with an atomization function and can generate ultrasonic vibrations. The liquid is ultrasonically refined into molecules by the first functional sheet 310, and then reaches the second functional sheet 321 to be further ultrasonically atomized into nano-scale particles and emitted. The double ultrasonic atomization process can make the emitted mist molecules finer.

In a specific embodiment, the first functional sheet 310 and/or the second functional sheet 321 has a deformation portion 3211, and the liquid through hole 311 is defined in the deformation portion 3211, as shown in FIGS. 11 to 13. A liquid storage chamber 350 is formed between the first functional sheet 310 and the second functional sheet 321 at a position corresponding to the deformation portion 3211, as shown in FIG. 13. After power is turned on, the first functional sheet 310 and the second functional sheet 321 resonate at the same frequency, so that the liquid in the liquid storage bottle stably enters the liquid storage chamber 350. The liquid enters the liquid storage chamber 350 through the liquid through hole 311 in the first functional sheet 310, and the liquid pressure in the liquid storage chamber 350 is reduced, which greatly reduces the possibility of oil leakage from the second functional sheet 321 (which is usually used for the atomization function); and the liquid storage chamber 350 can continuously provide a stable low-pressure liquid to the second functional sheet 321 which faces the outside, so that the pressure on the second functional sheet 321 facing the outside remains consistent, and no matter how much liquid is in the liquid storage bottle, it can ensure continuous misting and a stable misting amount, so that the spray is stable and not easy to be blocked.

The deformation part 3211 is a protrusion or depression formed on the first functional sheet 310 and/or the second functional sheet 321. In the embodiment shown in FIG. 13, the deformation part 3211 is disposed on the second functional sheet 321. In other embodiments, the structural design of the deformation part 3211 is not limited to a protrusion or a depression as long as the liquid storage chamber 350 is formed between the two metal sheets.

The second functional sheet 321 and the first transducer 322 are connected with paired electronic wires 340 and are electrically connected to the control circuit board 104. The liquid storage bottle 200 is in liquid communication with the atomizing assembly 300 so that the liquid can flow to the liquid through hole 311 of the first functional sheet 310. The shell 110 defines the first mist outlet 102, and the first through hole of the first transducer 322 of the atomizing assembly 300 is correspondingly connected to the first mist outlet 102.

The atomizing assembly utilizes high-frequency oscillation of the second functional sheet 321 to vibrate the liquid from the liquid storage bottle 200 into small particles that can be suspended in the air to produce naturally floating mist without the need for heating or adding any chemical reagents. The center of the second functional sheet 321 defines a plurality of atomization micropores, and the liquid flowing out of the liquid storage bottle 200 is atomized and then sprayed out from the atomization micropores to form a spray. An atomizing cavity 303 is formed between the front pressing plate 301 and the rear pressing plate 302, and a rubber (silicone) ring 330 is provided in the atomizing cavity. The silicone ring is used to seal a periphery of the second functional sheet 321 and the first transducer 322 in the atomizing cavity, prevent the liquid from flowing out from the periphery, while limit the atomized liquid to be sprayed out through the micropores of the second functional sheet. When in use, ultrasonic vibration is generated by the second functional sheet to break up the liquid molecules and generate naturally flowing mist which passes through a second mist outlet 3011 in the center of the front pressure plate 301 and then sprays out from the first mist outlet 102 of the shell 110. A liquid guide pipe 121 extends outward from the rear end of the rear pressure plate 302, and the tip of the liquid guide pipe 121 is connected to with interface connector. In the embodiment of the present invention, the front pressure plate 301, the rear pressure plate 302 and the rubber (silicone) ring 330 are all provided with through holes to facilitate the contact between the liquid flowing out of the liquid storage bottle 200 and the second functional sheet 321. The essential oil in the liquid storage bottle 200 flows out from the bottle mouth under gravity of the essential oil, flows through the liquid channel 123 in the connector 120 into the liquid guide pipe 121, then is transported into the atomizing cavity 303 and contacts the first functional sheet 310; when the aroma diffuser in operation, the first functional sheet 310, the second functional sheet 321 and the first transducer 323 resonate at the same frequency and generate the ultrasonic vibration, the essential oil is injected into the liquid storage chamber 350 through the liquid through hole 311 of the first functional sheet 310 and is atomized into mist under the ultrasonic vibration, the mist is then discharged out from the atomization micropores, passes through the second mist outlet 3011 and then sprayed out of the shell 110 through the first mist outlet 102.

In the embodiment of the present invention, the shell 110 includes an upper cover 111 and a bottom cover 112. The front pressure plate 301 is fixed in the shell 110 by bolts, and covers the first mist outlet 102.

In the embodiment of the present invention, the shell 110 is also provided with one or more buttons, which are electrically connected to the control circuit board 104. By pressing a switch button of the one or more buttons, the second functional sheet can be adjusted to start vibration, stop vibration, or change the vibration frequency.

The upper cover 111 is engaged with the upper end of the shell 110. The upper cover 111 is detachable to facilitate the replacement of the liquid storage bottle 200. The bottom cover 112 is fixed to the lower end of the shell 110 by bolts.

In the embodiment of the present invention, the power supply assembly 103 includes a power plug, a circuit board and a power supply shell. The circuit board is arranged in the power supply shell, and the power supply shell is fixed in the shell 110 by bolts. The power plug 106 is electrically connected to the circuit board, and the circuit board is electrically connected to the control circuit board 104 through a wire. The power supply assembly is set in the shell 110, which facilitates a compact structure of the atomizer 100, is scientific and reasonable and prolongs the service life of the aroma diffuser.

According to the working principle of the atomizer provided in the embodiment of the present invention, when in use, the essential oil in the liquid storage bottle flows to the rear pressure plate 302 through the liquid guide hose (liquid guide pipe) and then contacts the first functional sheet 310. The liquid first passes through the liquid through hole 311 of the first functional sheet 310 to reach the liquid storage chamber 350, and then the liquid is atomized under the ultrasonic vibration of the second functional sheet 321 and is emitted through the atomization micropores of the second functional sheet 321; or the first functional sheet 310 also has an ultrasonic vibration function, and the liquid is dispersed after being ultrasonically atomized by the first functional sheet 310 and the second functional sheet 321. The second functional sheet is used to vibrate the essential oil flowing out of the liquid storage bottle at high frequency to form small particles that can be suspended in the air, and then generating a naturally flowing mist that passes through the second mist outlet 3011 in the center of the front pressure plate 301 and is ejected from the first mist outlet 102 of the shell 110. Since the atomizing assembly has the first functional sheet 310, the pressure from the liquid in the liquid storage bottle is reduced, that is, the pressure of the liquid on the second functional sheet 321 is reduced, and the possibility of oil leakage of the second functional sheet (usually used for atomization function) is greatly reduced.

In the above-described embodiments, a battery may or may not be provided in the shell 110 of the atomizer 100. In some embodiment, no battery is provided in the atomizer 100, the atomizer 100 is powered through the power plug 106 connected to the mains supply. The power plug 106 is electrically connected to the control circuit board 104. In other embodiments, a battery is provided in the shell 110 of the atomizer 100, the battery may be a disposable battery or a rechargeable battery and is electrically connected to the control circuit board 104, and the atomizer 100 can be powered by the battery. If the battery is rechargeable, a charging interface is provided in the shell 110 for charging the battery, and the charging interface may use the power plug 106 or independently set.

The above description is only a preferred embodiment of the present invention and is not intended to limit the present invention. Any modifications, equivalent substitutions and improvements made within the spirit and principles of the present invention shall be included in the scope of protection of the present invention.

What is claimed is:

1. An aroma diffuser, comprising:

a shell, comprising:
- an upper cover; and
- a bottom cover connected to the upper cover, and defining a first mist outlet for spraying out essential oil mist;

a liquid storage bottle containing essential oil therein, mounted in the upper cover with a bottle mouth thereof facing downward, for supplying the essential oil by gravity;

a control circuit board installed in the bottom cover;

an atomizer assembly installed in the bottom cover, comprising:
- a first functional sheet, which is a circular metal sheet, defining a liquid through hole with a diameter of 2 mm or less;

a second functional sheet, which is a circular metal sheet with a protrusion forming a liquid storage chamber; wherein the second functional sheet is electrically connected to the control circuit board via a negative wire, and has one side attached to the first functional sheet; the liquid through hole of the first functional sheet serves as a liquid inlet, is located in and communicates with the liquid storage chamber, and is used to inject essential oil into the liquid storage chamber; and the protrusion defines atomization micropores in communication with the liquid storage chamber;

a first transducer, which is a piezoelectric ceramic transducer ring with a first through hole therein; wherein the first transducer is electrically connected to the control circuit board via a positive wire and is attached to the other side of the second functional sheet; the first transducer and the second functional sheet are combined to generate ultrasonic vibration to perform atomization; the protrusion of the second functional sheet is fitted in the first through hole of the first transducer; and a rubber ring, fixing and sealing peripheries of the first functional sheet, the second functional sheet and the first transducer; wherein the first functional sheet, the second functional sheet and the first transducer are resonantable at the same frequency;

an atomizing cavity for accommodating the atomizer assembly; wherein a front pressure plate and a rear pressure plate are snapped together to form the atomizing cavity therebetween; the first functional sheet, the second functional sheet and the first transducer are axially stacked between the front pressure plate and the rear pressure plate, and have the peripheries thereof tightly sealed and pressed between the front pressure plate and the rear pressure plate via the rubber ring; the front pressure plate defines a second mist outlet communicating the atomizing cavity with the first mist outlet; and the protrusion of the second functional sheet passes through the first through hole of the first transducer and protrudes toward the second mist outlet;

a connector, installed on a top open of the bottom cover, detachably connecting the bottle mouth of the liquid storage bottle, and defines a liquid channel therein which is communicated with the liquid storage bottle; and a liquid guide pipe, connecting the connector and the rear pressure plate, and in communication with the liquid channel of the connector and the atomizing cavity;

wherein the first functional sheet, the second functional sheet and the first transducer are arranged adjacent to each other; the essential oil in the liquid storage bottle flows out from the bottle mouth under gravity of the essential oil, flows through the liquid channel in the connector into the liquid guide pipe, then is transported into the atomizing cavity and contacts the first functional sheet; when the aroma diffuser in operation, the first functional sheet, the second functional sheet and the first transducer resonate at the same frequency and generate the ultrasonic vibration, the essential oil is injected into the liquid storage chamber through the liquid through hole of the first functional sheet and is atomized into mist under the ultrasonic vibration, the mist is then discharged out from the atomization micropores, passes through the second mist outlet and then sprayed out of the shell through the first mist outlet.

2. The aroma diffuser of claim 1, further comprising a second transducer; wherein the first transducer, the second functional sheet, and the second transducer are sequentially arranged in contact with each other; the second transducer defines a second through hole; the first transducer and the second transducer are electrically connected to the control circuit board via the positive wire, and the second functional sheet is electrically connected to the control circuit board via the negative wire.

3. The aroma diffuser of claim 1, wherein the connector has an annular wall accommodating and detachably connecting the bottle mouth of the liquid storage bottle.

4. The aroma diffuser of claim 3, wherein the upper cover and the bottom cover are respectively hollow cylindrical in shape; the shell further comprises a circular middle cover with a central opening; the middle cover is detachably installed between the upper cover and the bottom cover and accommodated in a space formed by the upper cover and the bottom cover; the annual wall of the connector is fitted in the circular middle cover; the bottle mouth of the liquid storage bottle extends into the connector through the central opening of the middle cover and is threadedly connected to the annular wall of the connector.

5. The aroma diffuser of claim 1, wherein the front pressure plate and the rear pressure plate are circular, fasten by side buckles and installed in the bottom cover; the rear pressure plate defines a hole therethrough in communication with the liquid guide pipe, the first functional sheet is located behind the rear pressure plate, the essential oil flows through the liquid guide pipe, then is transported to the first functional sheet through the hole of the rear pressure plate; and the first transducer is located behind of the front pressure plate with the first through hole facing the second mist outlet.

6. The aroma diffuser of claim 1, wherein the first mist outlet is opened in a side wall of the bottom cover; the front pressure plate is installed inside the bottom cover and is located behind the first mist outlet, and the second mist outlet aligned with the first mist outlet.

7. The aroma diffuser of claim 1, wherein the liquid through hole is defined in a center of the first functional sheet; the protrusion is formed in a middle of the second functional sheet, has a larger diameter than the liquid through hole and surrounds the liquid through hole;

the protrusion is in a shape of a circle; and the first through hole is defined in a center the first transducer, is a circular opening, and has a dimeter greater than that of the protrusion.

8. The aroma diffuser of claim 1, wherein the liquid guide pipe is a liquid guide hose with an upper end connected to the connector and a lower end thereof connected to the rear pressure plate.

9. The aroma diffuser of claim 1, wherein the rubber ring has an annular assembly groove on an inner side wall thereof, and the first functional sheet, the second functional sheet and the first transducer are installed in the assembly groove.

10. The aroma diffuser of claim 1, comprising a power plug electrically connected to the control circuit board; wherein the shell is provided with a power port for mounting the power plug.

* * * * *